United States Patent [19]

Mills et al.

[11] 4,121,575
[45] Oct. 24, 1978

[54] DEVICES FOR RAPID PLACEMENT AND RECORDING OF ECG PRECORDIAL LEADS IN PATIENTS

[76] Inventors: Harold Mills, 1049 Hillcrest Rd., Beverly Hills, Calif. 90210; Herbert Stein, 238 S. McCarty Dr., Beverly Hills, Calif. 90212

[21] Appl. No.: 729,797

[22] Filed: Oct. 5, 1976

[51] Int. Cl.² .............................................. A61B 5/04
[52] U.S. Cl. ......................... 128/2.06 E; 128/DIG. 4
[58] Field of Search .................... 128/2.06 E, 2.06 R, 128/2.06 V, 2.1 E, 404, 410, 411, 416, 417, 418, DIG. 4

[56] References Cited

U.S. PATENT DOCUMENTS

| 3,409,007 | 11/1968 | Fuller | 128/2.06 E |
|---|---|---|---|
| 3,498,291 | 3/1970 | Bunn | 128/2.06 E |
| 3,534,727 | 10/1970 | Roman | 128/2.06 E |
| 3,602,216 | 8/1971 | Moe, Jr. | 128/2.06 E |
| 3,610,229 | 10/1971 | Zenkich | 128/2.06 E |
| 3,631,851 | 1/1972 | Hesen | 128/2.06 R |
| 3,888,240 | 6/1975 | Reinhold, Jr. et al. | 128/2.06 E |
| 3,971,387 | 7/1976 | Mantell | 128/410 |
| 3,998,213 | 12/1976 | Price | 128/2.1 E X |

FOREIGN PATENT DOCUMENTS

| 1,355,600 | 2/1964 | France | 128/2.06 E |
|---|---|---|---|
| 6,700,019 | 7/1968 | Netherlands | 128/2.06 E |
| 274,612 | 7/1951 | Switzerland | 128/DIG. 4 |

OTHER PUBLICATIONS

Grais et al., "A 12-Lead Patient Cable for ECG Exercise Testing", Am. Heart J., Feb. 1974, vol. 87, No. 2, pp. 203–208.

*Primary Examiner*—Lee S. Cohen
*Attorney, Agent, or Firm*—Burns, Doane, Swecker & Mathis

[57] ABSTRACT

Method and apparatus for accurately and rapidly securing electrodes for electrocardiographic monitoring at correct anatomic precordial portions on patients having chests of significantly differing sizes and configurations. A piece of stretchable non-conductive material having apertures for the usual $V_1$ - $V_6$ positions is provided with removable electrodes and a device for retaining the material in a stretched position across the chest of a patient, the electrodes also being apertured to permit the introduction of an electrolyte.

19 Claims, 13 Drawing Figures

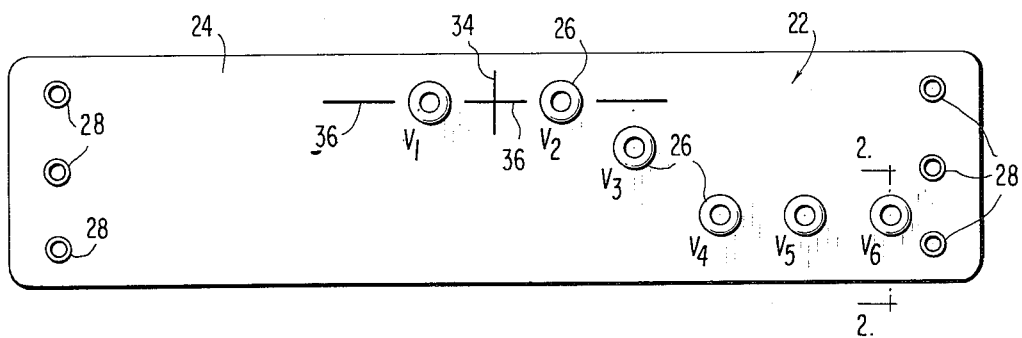
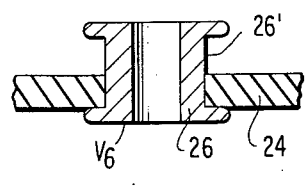
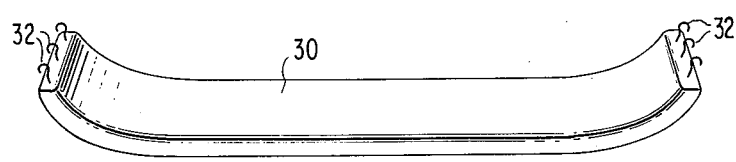
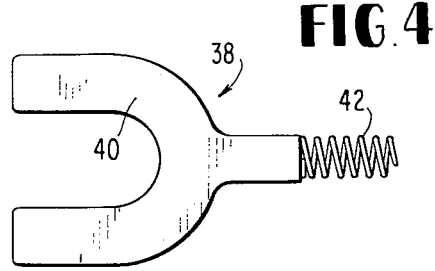
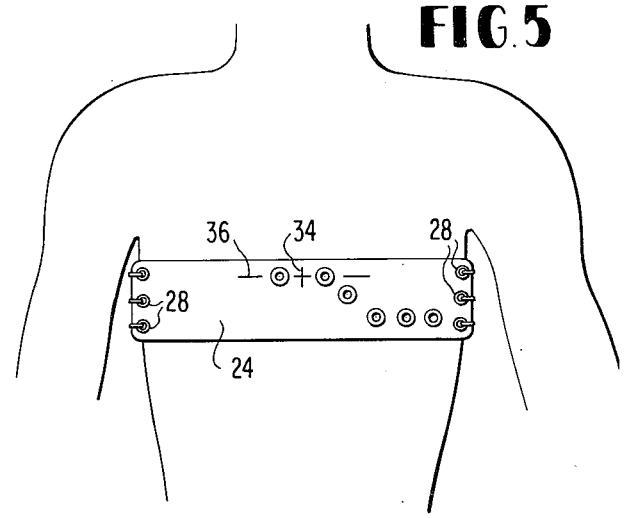
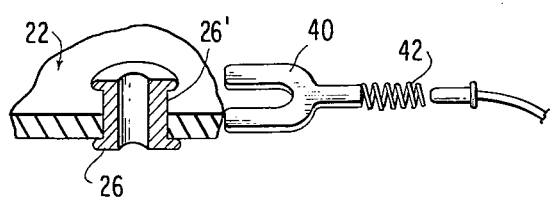
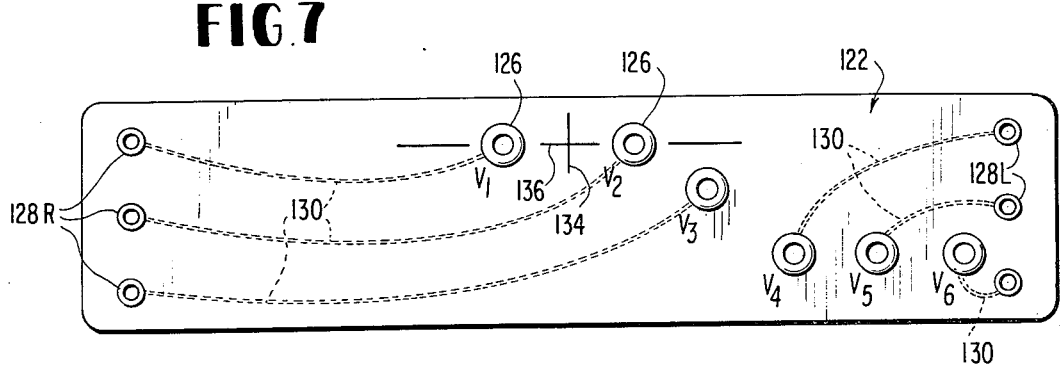

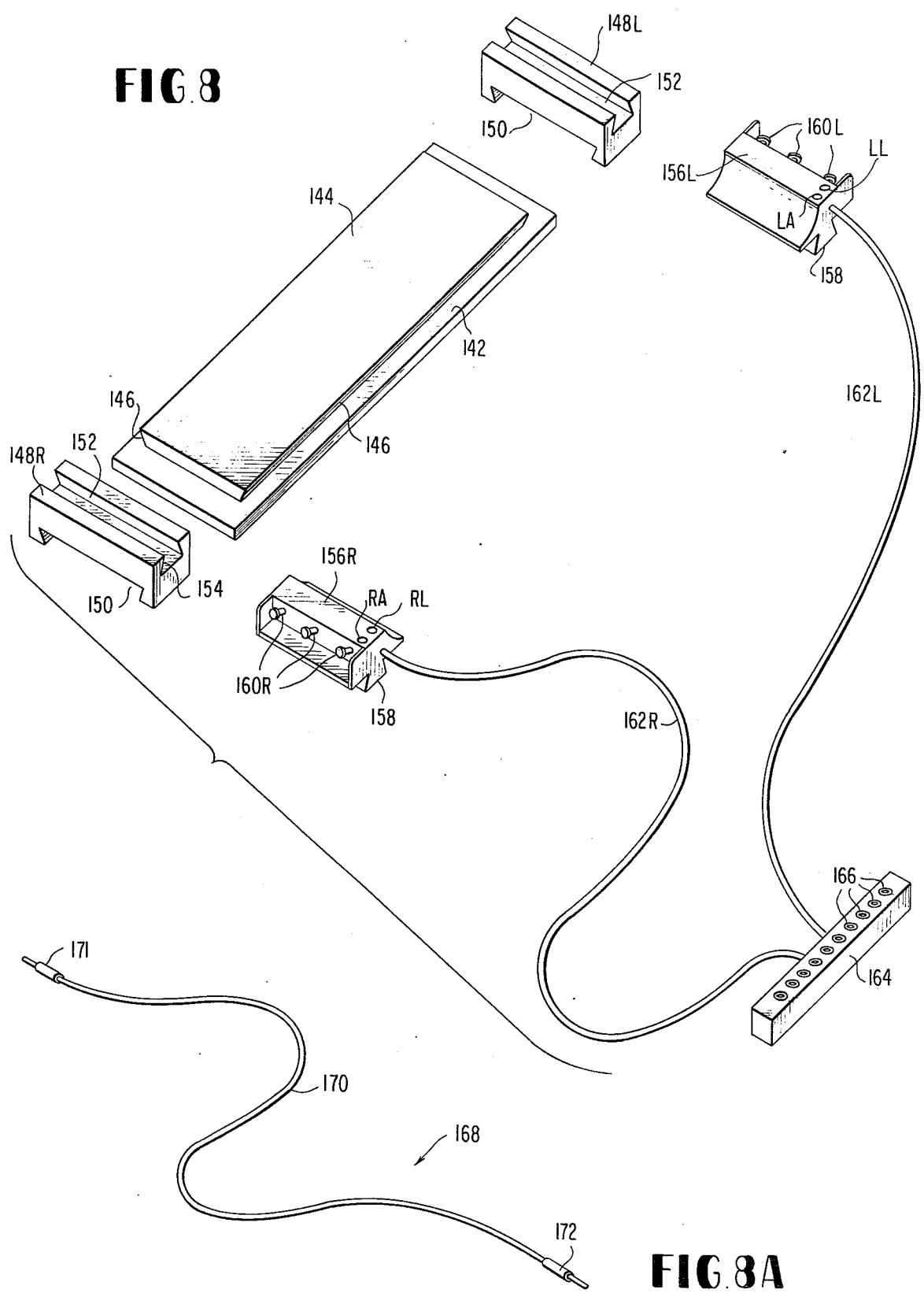

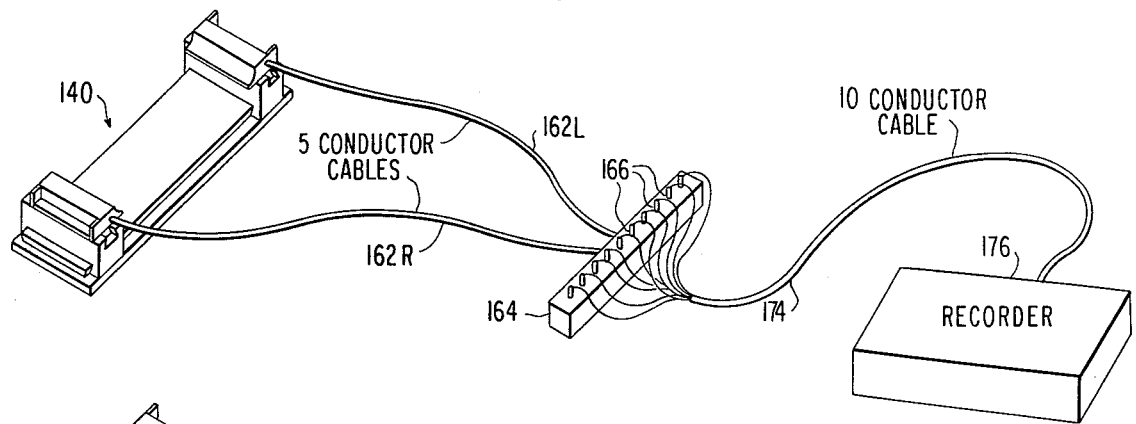
FIG.9
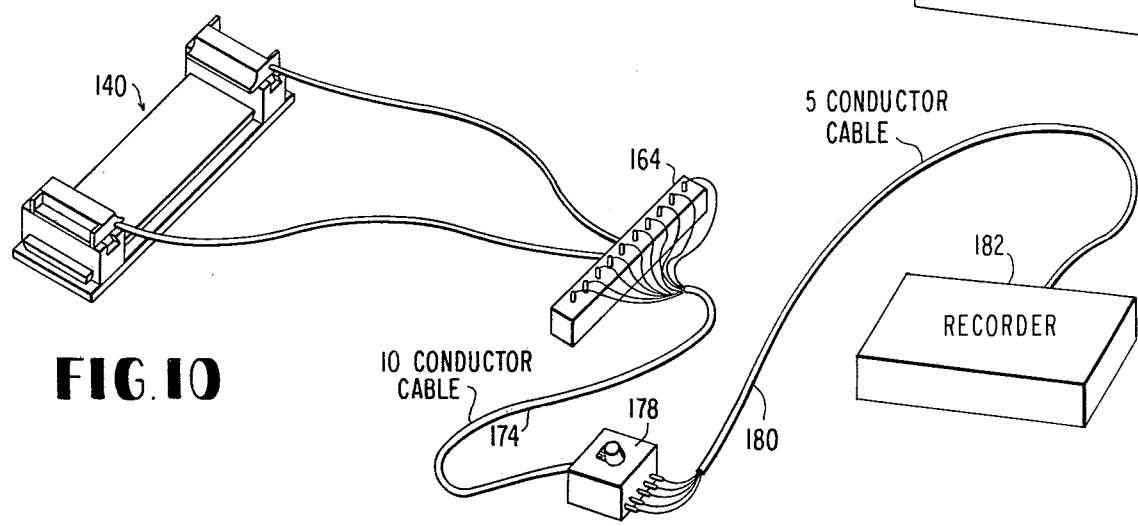
FIG.10
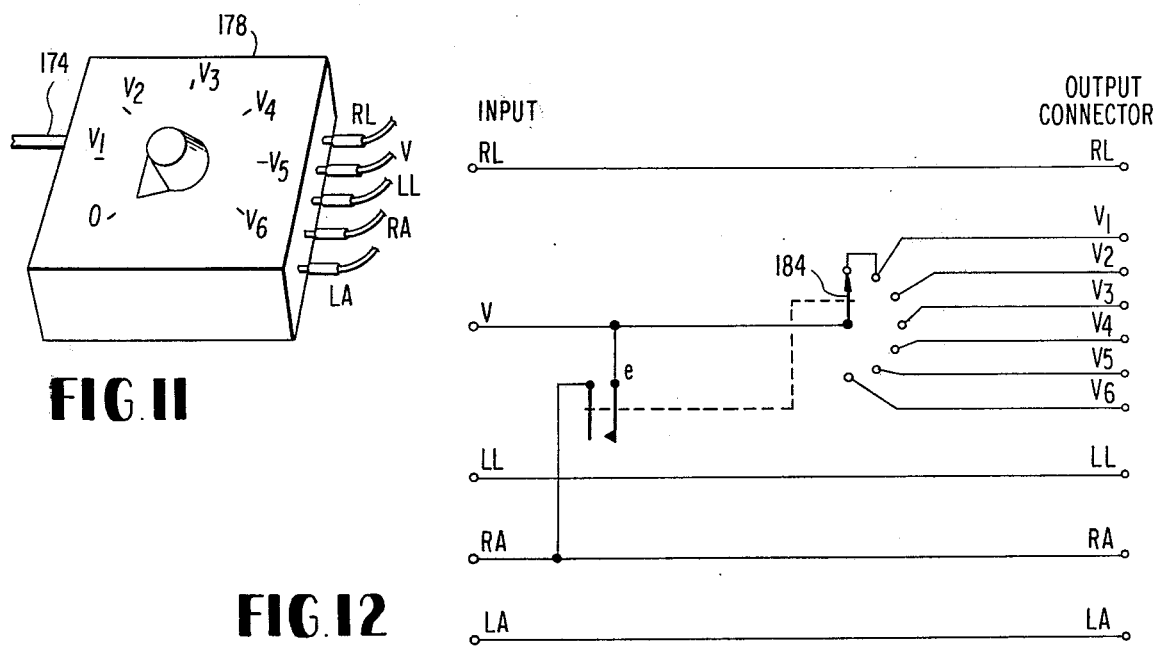
FIG.11
FIG.12

DEVICES FOR RAPID PLACEMENT AND RECORDING OF ECG PRECORDIAL LEADS IN PATIENTS

BACKGROUND OF THE INVENTION

The electrocardiogram (ECG) has proven over the years to be the single most effective clinical record for the diagnosis of cardiac muscle and cardiac nervous conduction abnormalities. An electrocardiogram is routinely taken not only on patients suspected of having cardiac disease but also on normal patients to establish base line cardiac data. Thus, millions of ECG tracings are recorded yearly in private physicians' offices and in hospitals. It is imperative that these tracings be reliable and also that they be obtained rapidly to minimize the cost. It is to these objectives that the present invention is directed.

Generally, the ECG is comprised of twelve distinct records (i.e., tracings) which are obtained from a combination of specific electrical signals obtained from the body of the patient. These signals result from the heart's electrical activity which is conducted throughout the body. The signals, ordinarily in the millivolt range, may be sensed by metal electrodes making electrical contact with the body by way of electrically conductive electrode paste. The signals are transmitted from the electrodes through cables to an electrocardiograph or ECG recorder which includes amplifying circuitry, a heat stylus writing mechansim and switching circuitry. The latter circuitry permits combining the signals ordinarily taken from ten different positions on a patient's body to obtain the twelve tracings ordinarily desired. The twelve tracings, ordinarily adequate to obtain the heart's full spectrum of electrical data, are obtained from electrodes placed on the patient's four extremities and six electrodes carefully positioned on the precordium (i.e., the chest wall of the heart area). The latter six electrodes in the precordial positions are designated as $V_1$, $V_2$, $V_3$, $V_4$, $V_5$ and $V_6$. In certain cases other positions on the chest may be chosen (e.g. $V_3R$) so that the specific example using positions $V_1$ to $V_6$ is illustrative rather than limiting.

The usual practice is to apply the electrodes to the arms (LA, RA), legs (LL, RL) and precordium ($V_1$, $V_2$, $V_3$, $V_4$, $V_5$ and $V_6$), with the electrodes being of a clamp type, suction cup type or adhesive type. Such electrodes must be applied one-at-a-time and, in the case of the precordial electrodes particularly require careful placing at specific anatomical locations. Thus, the careful and time consuming attention of a skilled nurse or doctor is required.

It is accordingly an object of the present invention to provide novel and improved method and apparatus for rapidly applying electrocardiograph electrodes to a patient's body in clinically acceptable anatomic regions.

Another object of the invention is to provide novel and improved method and means for applying the precordial electrodes simultaneously and in clinically acceptable anatomic areas on the patient's chest despite a wide range of chest sizes and configurations.

A further object of the invention is to provide novel and improved method and means for applying precordial electrodes in clinically acceptable positions on a patient's chest while facilitating the connection of leads to extremity electrodes to the electrocardiograph equipment.

An additional object of the invention is to provide novel and improved method and means for interconnecting leads from electrodes on a patient's body to electrocardiograph equipment.

These and other objects are attained by providing a chest piece including a strip of stretchable material with precordial electrodes spaced in clinically acceptable anatomic areas for a chest of small size and a holder for securing the strip in stretched position across a chest of larger size to cause the precordial electrodes to contact acceptable anatomic areas of that chest.

In a preferred embodiment, conductive connector rings at the ends of the chest piece may be individually connected electrically to the precordial electrodes. In addition, conductive connector hooks disposed on means on the holder for clamping the chest piece in position may be individually connected to conductors of a multi-conductor cable. The location of the connector hooks on the holder may be longitudinally adjustable to vary the amount the chest piece is stretched to conform with the size of the patient's chest. The hook means may also include terminals for receiving the ends of leads from electrodes on the extremities (arm and leg) on the corresponding side of the patient and these terminals may be connected to additional conductors in the multi-conductor cables.

The holder may be in the form of a strip having first slidable bars slidably adjustable longitudinally thereof, with each of these bars including another slidable bar slidably adjustable in a transverse direction.

The multi-conductor cables from both holder hook means, or transversely adjustable, may be connected to a terminal block. This block may have ten terminals representing connections respectively to the four extremity electrodes RA, LA, RL and LL and the six precordial electrodes $V_1$, $V_2$, $V_3$, $V_4$, $V_5$ and $V_6$. Where the tracings of a monitoring operation are to be connected to a five-lead (RA, RL, LA, LL and V) electrocardiograph recorder, an adapter switch box may be provided between the connecting block and the recorder so that switching between the six precordial leads may be made directly at the switch box. This switch box is also useful for increasing the speed and convenience of using a five-lead or single V-channel recorder even where the input leads of the switch box are connected to the various electrodes by other arrangements than the novel chest piece of the present invention.

BRIEF DESCRIPTION OF THE DRAWINGS

FIG. 1 is a plan view of one embodiment of a chest piece for establishing anatomically acceptable precordial electrode positions for connection to electrocardiograph apparatus;

FIG. 2 is an enlarged vertical sectional view taken along the line 2—2 of FIG. 1;

FIG. 3 is a plan view of one embodiment of a holder for securing the chest piece of FIG. 1 to the chest of a patient;

FIG. 4 is an enlarged pictorial view of one embodiment of a spring connector for use with the chest piece of FIG. 1;

FIG. 5 is a pictorial view of the chest piece of FIG. 1 secured to the chest of a patient by the holder of FIG. 3;

FIG. 6 is an enlarged plan view showing the connection of the spring connector of FIG. 4 to the chest piece of FIG. 1;

FIG. 7 is a plan view of a second embodiment of a chest piece;

FIG. 8 is an exploded pictorial view of a second embodiment of a holder for use with the chest piece of FIG. 7;

FIG. 8A is a view of one embodiment of a connector wire for use with the chest piece of FIG. 8;

FIG. 9 is a pictorial view schematically illustrating the connections of the holder of FIG. 8 to a ten terminal electrocardiograph recorder;

FIG. 10 is a pictorial view schematically illustrating the connections of the holder of FIG. 8 to a five terminal electrocardiograph recorder;

FIG. 11 is a pictorial view of one embodiment of an adaptor for use with a five terminal electrocardiograph; and, FIG. 12 is a schematic circuit diagram of the adaptor of FIG. 11.

DETAILED DESCRIPTION OF PREFERRED EMBODIMENTS OF THE INVENTION

As illustrated in FIG. 1, a chest piece 22 may comprise a strip 24 of expandable or stretchable material such as rubber sheeting. Extending through the strip 24 are six spaced electrodes designated $V_1$, $V_2$, $V_3$, $V_4$, $V_5$ and $V_6$ in accordance with their positions. As best shown in the enlarged sectional view through the electrode $V_6$ in FIG. 2, each electrode may comprise a hollow metal sleeve or rivet member 26 extending through the strip with the outer end (away from the patient's skin) projecting beyond the adjacent surface of the strip at 26' to facillitate the attachment of leads as will be discussed below. At each end of the strip 24, three transversely spaced connector rings 28 are shown extending through the strip 24.

With reference to FIG. 3, a holder 30 is preferably formed of rigid wood or plastic material or the like although it might in certain circumstances be of flexible fabric or other material. The holder may include hooks 32 at each end corresponding in number and spacing to the connector rings of the chest piece of FIG. 1. The holder 30 extends around the back of the patient so that the hooks 32 thereon may engage the connector rings 28 of the chest piece to hold the latter in place across the chest of the patient as shown in FIG. 5.

A significant feature of the construction thus far described is the disposition or location of the electrodes $V_1$ to $V_6$ on the chest of the patient. With the strip 24 of the chest piece in an unstretched condition, these electrodes are spaced suitably for engagement with the correct anatomic contact areas for the precordial electrodes usually designated $V_1$, $V_2$, $V_3$, $V_4$, $V_5$ and $V_6$ on a chest of small size such as that of a ten year old child. To facilitate positioning on the patient, the strip of the chest piece may be provided with a vertical line or mark 34 indicating the location for the mid-chest or mid-sternum line and a horizontal mark 36 indicating the location of the mid-nipple line. Thus, the vertical line is midway between the electrodes $V_1$ and $V_2$ and the horizontal line is in alignment with these electrodes.

With the basic pattern for the electrodes based on the measurements of a small chest as stated, the electrodes can be made to automatically assume the correct anatomic location on a larger chest by stretching the stretchable strip 24 the appropriate amount in securing it to the patent. This is readily accomplished by employing holders 30 of different sizes, or with multiple hook locations, for securing the chest piece in place on different size chests. Alternatively, elastic strips of different flexibility might be used as a holder. In the preferred embodiment shown in FIG. 8, the chest piece is held in place by means of a rigid holder with longitudinally and transversely adjustable hook members.

FIG. 4 shows a conductor 38 including a U-shaped spring connector 40 for engaging electrodes 26 at the aforementioned projecting portion 26' as shown in FIG. 6. The hollow construction of electrodes 26 permits the introduction of conductive electrode paste from the outside of the passage therethrough to the other end which contacts the skin of the patient so as to provide a low-resistance contact between the electrode and the patient's skin. The other end of the conductor 38 may be provided with a spring wire adaptor 42 or other suitable conventional connector for receiving a metal pin connector at the end of a lead wire of the patient cable of an electrocardiograph recorder. A single conductor 38 may be moved from one electrode $V_1$ to $V_6$ to another or conductors may be connected to all the electrodes simultaneously for operation through an adaptor unit such as is hereinafter described in connection with FIGS. 11 and 12.

FIGS. 7 and 8 illustrate, respectively, a chest piece and a holder adapted for joint use in a particularly preferred embodiment of the invention. With reference to FIG. 7, the chest piece includes a strip 122 of stretchable material similar to the strip 24 of FIG. 1 and is provided with electrodes 126 spaced therein in accordance with the appropriate precordial anatomic positions $V_1$, $V_2$, $V_3$, $V_4$, $V_5$ and $V_6$ for a patient having a small chest. Also, like the chest piece of FIG. 1, the chest piece of FIG. 7 is stretchable across the chest of a larger patient to automatically adjust the spacing of the electrodes 126 to cause them to engage the corresponding precordial anatomic positions for persons having larger chests. Three connecting rings 128L and 128R are shown secured at the left and right ends, respectively, of the strip 122 for engagement by hooks on corresponding positions on a holder member to be described in connection with FIG. 8.

The chest piece 122 includes electrical conductors 130 individually making electrical connection between the six metal electrodes 126 and the end connectors 128L and 128R. In FIG. 7, the electrodes at precordial positions $V_1$, $V_2$ and $V_3$ are shown connected by the conductors 130 to the connector rings 128R for the patient's right side, which rings are labelled $V_1$, $V_2$ and $V_3$, respectively. Similarly, the electrodes at positions $V_4$, $V_5$ and $V_6$ are connected, respectively, to the connector rings 128L on the patient's left side designated $V_4$, $V_5$ and $V_6$. The electrical conductors 130 interconnecting the electrodes and connector rings are preferably embedded in the stretchable or elastic strip 122, although they may be disposed on the surface of the strip opposite the surface which contacts the patient's skin. It is also preferred that the conductors be made flexible, as by employing a slight helical or curved configuration, so that they may accommodate to the changes in spacing of the interconnected electrodes and connector rings when the chest piece is stretched to the different lengths necessary for use in patient's having chests of different sizes.

The electrodes 126 may be hollow sleeve members extending through the chest piece strip similarly to the electrodes 26 of FIGS. 1 and 2, whereby electrically conductive electrode paste can be conveniently introduced into them from the outside after the chest piece is installed to obtain a low-resistance contact with the patient's body. Because of the internal electrical connections to the connector rings, the electrodes 126 do not necessarily require outwardly projecting portions such as are shown at 26' in FIG. 2.

The chest piece 122 is provided with a mid-sternum line 134 and a mid-nipple line 136 for facilitating proper positioning as described in connection with the chest piece of FIGS. 1 and 2.

FIG. 8 shows a holder for location at the back of a patient to hold the chest piece in an adjustable position according to the size and conformation of his chest and facilitate making the necessary electrical connection to electrocardiograph recorder equipment.

The holder includes a holder base plate 142, preferably of rigid plastic material including an outwardly projecting longitudinal bar 144 having downwardly and inwardly extending bevelled sides 146. Longitudinal bar members 148R and 148L have bottom slots 150 making a sliding fit over the longitudinal bar 144 and further include transverse upper slots 152 with upwardly converging, bevelled edges 154. Transverse bar members 156R and 156L are provided with corresponding projections fitting into the slots 152 for transverse sliding adjustment therein.

Bar 156R includes three metal hooks 160R, designated $V_1$, $V_2$ and $V_3$, each connected to one of the wires in a five-wire cable 162R. Also two pin jacks RA (right arm) and RL (right leg) are disposed on bar 156R and connected to the other two wires of five-wire cable 162R. In like manner, bar 156L includes three hooks, designated $V_4$, $V_5$ and $V_6$ and two pin jacks LA (left arm) and LL (left leg) connected individually to five wires in five-wire cable 162L. The remote ends of five-wire cables 162R and 162L extend into a terminal or connector block 164 of non-conductive material with the ten wires of the cables terminating in ten binding posts 166.

The construction of the holder is such that the engagement of the slots 150 of bars 148R and 148L with the base plate 142 and the engagement of the slots in the bars 148R and 148L with the projections on the transverse bars 156R and 156L is loose or frictionless to provide free movement or the chest piece pulls the sliding bars of the holder together until they touch the sides of the chest. The adjustable bars will hold their adjusted positions with the chest piece 122 stretched the desired amount and in the desired transverse position through the pull of the chest piece.

In use, bars 148R and 148L are assembled on bar 144 with their slots 150 in longitudinally adjustable engagement with longitudinal bar 144. Also projections 158 on transverse bars 156R and 156L are fitted into transverse slots 152 in bars 148R and 148L, respectively, for slidable transverse adjustment therein. The chest piece is placed over the chest of the patient and the holder under the back of the patient. The connector rings 128R and 128L are engaged with hooks 160R and 160L, respectively. With the aid of the mid-sternum and mid-nipple lines 134 and 136 on the chest piece 122, the blocks 148R and 148L and 156R and 156L are slidably adjusted to so stretch the flexible or stretchable strip of the chest piece as to locate the respective electrodes 126 at the correct percordial anatomic positions corresponding to $V_1$, $V_2$, $V_3$, $V_4$, $V_5$ and $V_6$ for the particular chest size of the patient.

FIG. 8A illustrates a connector wire 168 for use in connecting the pin jacks RA, RL, LA and LL to the extremities of the patient. One end of a wire 170 terminates in a minature plug 171 for engagement with the aforementioned pin jacks while the other end is provided with a standard ECG plug 172 for engagement with extremity electrodes which may of conventional type.

With the chest piece and holder assembled on the patient as described, and the pin jacks RA, RL, LA and LL connected through wire connectors 168 to extremity electrodes on the right arm, right leg, left arm and left leg, respectively, the binding posts 166 of the connector block 164 for the holder will provide connections to each of the four extremity positions and each of the six usual precordial positions. It will be seen that the structure offers particular convenience in making connections to the four extremities in addition to providing automatic connections to the correct anatomic precordial positions.

FIG. 9 shows schematically the electrical connections of the preferred form of the invention shown in FIGS. 7 and 8 to a ten-terminal electrocardiograph conductor. Thus, the five-wire leads 162R and 162L from the holder 140 are connected to the terminal block 164 and the ten binding posts 166 from the block are connected by a ten conductor cable 174 to the electrocardiograph 176. The usual electrocardiogram tracings can then be made by the electrocardiograph recorder without any change of connections or switching of the auxiliary connecting equipment.

When the chest piece and holder of FIGS. 7 and 8 are used with a five-terminal electrocardiograph recorder, the electrical connections are made as shown in FIG. 10. In this Figure, a ten conductor cable 174 extends from the terminals 166 of block 164 to an adaptor switch 178 from which a five conductor cable of the type conventionally provided with five terminal electrocardiograph.

FIGS. 11 and 12 show the adaptor as including five output conductors extending to the five terminal, single V channel electrocardiograph recorder. Four of these conductors extend directly through the adaptor to the four extremity conductors RL, LL, RA and RL while the fifth conductor is the V channel conductor which may selectively be connected to each of the precordial leads $V_1$ to $V_6$. A manually controlled selector 184 is movable from a zero positon 0 through connections to the leads $V_1$ to $V_6$. With this selector switch used in conjunction with a five-terminal electrocardiograph recorder, the selector switch 178 is the only peripherial equipment which must be operated to provide the usual electrocardiogram tracings once the external connections to the terminal block 164 have been made.

From the foregoing description, it will be apparent that the present invention provides a number of features which increase the ease and speed with which electrocardiograms can be made and at the same time decrease the chance of errors and reduce the cost. The stretchable chest piece provides a means for rapidly locating the precordial electrodes at the correct anatomic position on a patient's chest, whether used with holders of different sizes or with adjustable holders. The advantages of the construction are further enhanced when the precordial electrodes are electrically connected with end connector means and through those means to connectors associated with the holder. The preferred holder construction of FIG. 8 permits ease of longitudinal and transverse adjustment of the chest piece mechanically as well as electrical connection to the patient's extremities as well as to the precordial electrodes. The adaptor as particularly shown in FIGS. 11 and 12 not only facilitates using a five-conductor, single V channel electrocardiograph recorder with the presently disclosed chest piece and holder but offers similar advantages in use with conventional means for making the electrode connections to the patient.

The chest piece of FIG. 7 is preferably used with the holder of FIG. 8 which provides transversely as well as longitudinal adjustment of the position of the six connecting hooks for making connection to the precordial electrodes and jacks for making convenient connection to the corresponding right and left side terminal electrodes. However, a simplified holder may be used with hooks making connection to the precordial electrodes and with conductors associated with the holder for making connection thereto without special provisions for transverse adjustments or connections through the holder or a cable therefrom to extremity electrodes. Various other varistions will appear to those skilled in the art from the foregoing description.

The present embodiments are therefore to be considered in all respects illustrative and not restrictive, the scope of the invention being indicated by the appended claims rather than by the foregoing description, and all changes which come within the meaning and range of equivalency of the claimed are therefore intended to be embraced therein.

What is claimed is:

1. An electrocardiograph electrode assembly device for automatically positioning a plurality of electrodes in the correct anatomical position on the chests of patients having significant differences in size comprising:

a chest piece including a strip of stretchable, non-conductive material, a plurality of electrodes each adapted for making an electrical connection with an electrocardiograph and each carried by said strip in a position to contact a precordial anatomic position for electrocardiograph monitoring when the strip is disposed in a substantially unstretched condition on the chest of a first patient with the ends thereof in a predetermined position relative to his chest, and first connecting means carried by said strip adjacent each end thereof, said non-conductive material having sufficient stretch between said electrodes to automatically position each of said electrodes in the correct anatomical position for electrocardiograph monitoring when said strip is stretched over a chest larger than the chest of the first patient to position the ends thereof in a predetermined position relative to the chest of the patient; and, a holder adapted to be positioned behind a patient and having second connecting means for engaging said first connecting means on said chest piece to hold said strip in a predetermined position relative to the chest of a patient when said first and second connecting means are engaged.

2. An electrocardiograph electrode assembly device as recited in claim 1 wherein each of said electrodes comprises a metal member having a hollow cavity extending through said strip, whereby an electrolyte may be inserted to establish a low resistance electrical connection between the electrode and the chest of a patient when the chest piece is positioned on the patients' chest.

3. An electrocardiograph electrode assembly device as recited in claim 1 wherein each of said electrodes is removably carried by said strip so that new electrodes may be used for different patients.

4. An electrocardiograph electrode assembly device as recited in claim 1 wherein:

said first connecting means includes plural connectors which are electrically conducting and each individually connected electrically to one of said electrodes;

wherein said second connecting means includes plural connectors which are electrically conductive and adapted for making an electrical connection with an electrocardiograph.

5. A chest piece for automatically locating the position of electrocardiograph electrodes on the chest of a patient comprising:

a strip of stretchable, non-conductive material adapted for positioning on the chest of a patient undergoing electrocardiographic monitoring with the ends thereof in predetermined location relative to the chest of the patient;

a plurality of electrodes carried by said strip in predetermined locations thereon, each of said electrodes being positioned for contacting a precordial anatomic position of the patient for electrocardiographic monitoring when positioned in a substantially unstretched condition on the chest of a first patient having a chest of relatively small size; and, connecting means carried by said strip at opposite ends thereof for stretching said strip to locate the ends thereof in said predetermined positions relative to the chest of the patient to thereby increase the spacing between each of said electrodes to position them in the correct precordial anatomic positions for electrocardiographic monitoring on a chest larger in size than the chest of said first patient.

6. A chest piece for an electrocardiograph electrode assembly device as recited in claim 5 wherein each of said electrodes comprises an electrically conductive electrode member having a hollow cavity extending through said strip to facilitate the insertion of an electrolyte into contact with the electrode and the patients' chest.

7. A chest piece for an electrode assembly device as recited in claim 6 wherein each of said electrode members includes a portion projecting beyond one surface of said strip for engagement by an electrical connector.

8. A chest piece as recited in claim 5 wherein each of said electrodes is removably carried by said strip so that new electrodes may be used for different patients.

9. A holder for an electrocardiograph electrode assembly comprising:

an elongated member adapted to be positioned laterally across the back of a patient in engagement therewith;

positioning means carried by said elongated member adjacent each end thereof, said positioning means being adjustably positionable with respect to said elongated member in a lateral direction across the back of the patient and in a direction longitudinally of the patient;

mechanical connector means carried by said positioning means for engaging an electrocardiograph electrode assembly disposed across the chest of the patient; and, electrical connector means carried by said positioning means, said electrical connector means being adapted to establish an electrical connection between the electrodes of an electrocardiograph electrode assembly when engaged by said mechanical connector means and an electrocardiograph.

10. The holder of claim 9 wherein said mechanical connector means and said electrical connector means comprise a common set of electrically conductive connectors having sufficient strength to withstand the tension applied by engagement with an electrocardiograph electrode assembly.

11. A method of automatically positioning electrocardiograph electrodes on the chest of patients of significantly different chest sizes in anatomic precordial locations comprising the steps of:
providing a stretchable chest piece having a plurality of electrodes positioned with respect to each other when the chest piece is unstretched and centered on the chest of a patient of relatively small size to conform to the anatomic precordial locations on the chest of the patient;
stretching the chest piece across the chest of a patient of a relatively large size to place the ends thereof in a predetermined relationship with respect to the chest of the patient while monitoring the chest piece centered with respect to the patient's chest to thereby stretch the distance between the electrode locations so that the stretching of the chest piece between the electrode locations automatically effects the positioning of the electrodes in the anatomic precordial locations on the chest of the patient with a larger chest size.

12. The method of claim 11 wherein each of the electrocardiograph electrodes include a passage extending through the chest piece and including the further steps of establishing a low impedance electrical connection between the electrodes and the chest of the patient by applying an electrolyte to the exposed end of the passage.

13. A holder for an electrocardiograph electrode assembly comprising:
an elongated member adapted to be positioned laterally across the back of a patient in engagement therewith;
positioning means carried by said elongated member adjacent each end thereof, said means being adjustably positionable with respect to said member in a lateral direction across the back of the patient and in a direction longitudinally of the patient; and
mechanical connector means carried by said positioning means for engaging an elastic electrocardiograph electrode assembly disposed across the chest of the patient, the lateral positioning of said positioning means being responsive to the elasticity of the electrocardiograph electrode assembly.

14. The holder of claim 13 wherein said positioning means includes first and second means relatively movable in a direction longitudinally of the patient, said first means being slidably carried by said elongated member for relative movement with respect thereto in a direction laterally of the patient.

15. Apparatus for automatically locating the position of a plurality of electrocardiograph electrodes on the chest of patients of significantly different chest sizes in anatomic precordial locations comprising:
a strip of non-conductive material adapted for positioning on the chest of a patient,
said strip having means for identifying at least two predetermined positions thereon corresponding to a like numbered position on the chest of any patient,
said strip having a narrow dimension greater than the distance longitudinal of the patient between anatomic precordial locations for patients of significantly differing sizes,
said strip having a longitudinal dimension sufficient to permit positioning of said at least two identified predetermined positions on the corresponding positions on the chest of a patient of relatively small size with the strip in a substantially unstretched condition but insufficient to permit positioning of said at least two predetermined positions on the corresponding positions on the chest of a patient of relatively large size with the strip in said substantially unstretched condition,
said strip having a plurality of apertures in predetermined positions with respect to each other and to said at least two predetermined positions with said strip in an unstretched condition,
said strip being stretchable in a longitudinal direction sufficiently to position said at least two identified predetermined positions on corresponding positions on the chest of a patient of relatively large size,
the stretchable nature of the strip allowing the spacing between adjacent ones of said plurality of apertures to vary as a function of the stretching of said strip so that the position of said plurality of apertures locates the anatomic precordial positions on the chest of the patient of relatively large size on which said strip is adapted to be positioned.

16. The apparatus of claim 15 wherein said plurality of apertures is at least six.

17. A method of automatically determining the anatomic precordial location on the chest of patients having significantly different chest sizes comprising the steps of:
providing a chest piece of stretchable material having at least two predetermined positions identifiable as corresponding to a like number of predetermined positions on chests of significantly differing sizes, and carrying indicia of a plurality of anatomical precordial positions;
stretching the chest piece to position the predetermined positions of the chest piece on the corresponding positions on the chest of the patient; and,
determining a plurality of anatomical precordial locations on the chest of the patient by reference to the indicia carried by the chest piece.

18. The method of claim 17 wherein the indicia carried by the chest piece includes a plurality of metallic electrodes adapted to contact the chest of the patient when the chest piece is in place on the chest of the patient.

19. The method of claim 18 wherein each of the plurality of electrodes defines a passageway through the chest piece; and,
including the further step of depositing an electrolyte into the passageway defined by the electrodes.

* * * * *